(12) United States Patent
Kealy

(10) Patent No.: US 6,261,591 B1
(45) Date of Patent: Jul. 17, 2001

(54) METHOD FOR REDUCING HIP JOINT LAXITY

(75) Inventor: Richard D. Kealy, Waterloo, IL (US)

(73) Assignee: Ralston Purina Company, St. Louis, MO (US)

( * ) Notice: Subject to any disclaimer, the term of this patent is extended or adjusted under 35 U.S.C. 154(b) by 0 days.

(21) Appl. No.: 09/247,763

(22) Filed: Feb. 9, 1999

(51) Int. Cl.[7] .................. A61K 31/66; A61K 33/42; A01N 57/00; A01N 59/26; C12P 3/00
(52) U.S. Cl. ............... 424/442; 424/57; 424/601; 424/603; 435/168; 514/75
(58) Field of Search .................... 435/168; 424/603, 424/57, 442, 601; 514/973, 75

(56) References Cited

U.S. PATENT DOCUMENTS

| | | | |
|---|---|---|---|
| 4,039,689 | 8/1977 | Bone | 426/99 |
| 4,044,158 | 8/1977 | Burkwall, Jr. | 426/271 |
| 4,127,678 | 11/1978 | Burkwall, Jr. . | |
| 4,215,149 | 7/1980 | Majlinger | 426/292 |
| 4,267,195 | 5/1981 | Boudreau et al. | 426/2 |
| 4,276,311 | 6/1981 | Burrows et al. | 426/56 |
| 4,444,796 | 4/1984 | Ueno et al. . | |
| 4,514,431 | 4/1985 | Buckholz, Jr. et al. | 426/641 |
| 4,772,476 | 9/1988 | Kealy et al. . | |
| 4,784,862 | 11/1988 | Wotherspoon | 426/103 |
| 4,806,340 | 2/1989 | Gaffar et al. | 424/52 |
| 5,000,940 | 3/1991 | Staples et al. . | |
| 5,000,943 | 3/1991 | Scaglione et al. . | |
| 5,000,973 | 3/1991 | Scaglione et al. . | |
| 5,011,679 | 4/1991 | Spanier et al. . | |
| 5,015,485 | 5/1991 | Scaglione et al. . | |
| 5,047,231 | 9/1991 | Spanier et al. . | |
| 5,094,870 | 3/1992 | Scaglione et al. . | |
| 5,114,704 | 5/1992 | Spanier et al. . | |
| 5,186,964 | 2/1993 | Gierhart et al. | 426/74 |
| 5,296,209 | 3/1994 | Simone et al. | 424/49 |
| 5,296,217 | 3/1994 | Stookey | 424/57 |
| 5,391,743 | 2/1995 | Ebetino et al. . | |
| 5,618,518 | 4/1997 | Stookey | 424/57 |

*Primary Examiner*—Deborah K. Ware
(74) *Attorney, Agent, or Firm*—Armstrong Teasdale LLP

(57) ABSTRACT

Nutritionally balanced dog food compositions containing a dietary source of pyrophosphate, for reducing the incidence and extent of hip joint subluxation in dogs, and method of use. One embodiment of the dog food composition includes about 2.0% by weight sodium acid pyrophosphate. In use and in one embodiment of the method a puppy is fed the dog food composition as substantially the sole diet from weaning at about 6–8 weeks of age to about 2 years of age, to improve hip joint stability and reduce the incidence and severity of canine hip dysplasia.

11 Claims, No Drawings

METHOD FOR REDUCING HIP JOINT LAXITY

FIELD OF THE INVENTION

This invention relates generally to methods for reducing hip joint laxity in animals and more particularly, to dog food compositions and feeding methods which reduce the incidence and severity of hip dysplasia and osteoarthritis in dogs.

BACKGROUND OF THE INVENTION

Canine hip dysplasia (CHD) is a common problem in veterinary medicine. CHD is a coxofemoral joint deformity which is not apparent at birth but develops during puppyhood, frequently resulting in severe arthritic pain and immobility. CHD occurs among many breeds of dogs, but has a higher incidence and severity among larger dog breeds having an average adult body weight of 35 pounds or more. Generally, the larger the size of a breed, the higher the incidence of CHD.

The principal clinical symptom of CHD is subluxation of the hip joint, an indicator of hip joint laxity, which causes abnormal wear and degeneration of hip joint tissue. Laxity of the hip joint begins a cycle in which movement by the animal forces the femoral head into an abnormal position in the joint. The abnormal positioning of the femoral head causes erosion of the joint cartilage and inflammation of the synovial membrane surrounding the joint. The end result of chronic joint laxity is an abnormally shallow acetabulum and a flattened femoral head, resulting in joint pain, instability and immobility. A similar mechanism is involved in the development of osteoarthritis. Research has shown that reduction of hip joint laxity during early growth helps to prevent the development of CHD and osteoarthritis in dogs.

Research also suggests a correlation between accelerated bone growth during the first nine months of puppyhood, and the development of CHD. The first nine months of life are considered to be a critical period for hip joint development in the dog. During this period the acetabulum is growing at an accelerated rate relative to the femoral head. The accelerated growth rate renders the acetabulum more plastic and particularly susceptible to malformation under the influence of hip joint laxity. It ha; been postulated that reduction of overall bone growth rate during the first nine months of life can improve hip joint congruity by reducing the disparate growth rate between the acetabulum and the femoral head.

Typically, diagnosis of CHD is accomplished by standard radiographic methods, which are approximately 70% accurate overall, with increasing accuracy of diagnosis the closer the animal is to 2 years of age. Radiographic diagnosis relies on a finding of subluxation of the feinoral head. The severity of CHD as deduced from clinical presentation does not always correlate well with actual radiographic measurements because of the confounding influence of individual and breed variations in temperament and body structure.

CHD has a genetic basis, with heritability most frequently estimated to be about 0.30. For example, a heritability of about 0.3 indicates that about 30% of the variation in occurrence of CHD is attributed to parentage, while the remaining 70% is attributable to environmental factors or interactions with environmental factors. The exact nature of the environmental factors which affect CHD incidence and severity is not known for certain, and clinically the disease is highly variable among individual dogs. However, evidence supports the contention that diet and feeding are significant factors affecting hip joint laxity and the development of CHD, and suggests that manipulation of diet, especially during the early stages of bone development, might be one way to treat CHD. Dietary methods for treating CHD are especially attractive because typically they are easily practiced.

A known dog food composition and feeding method exists for reducing hip joint instability in dogs. The composition has a specified dietary anion gap (DAG) of no more than about 20 milliequivalents/100 g of food. Dietary anion gap is calculated as: Na (mEq/100 g)+K (mEq/100 g)−Cl (mEq/100 g). The feeding method relies on administration of the composition during the early years of growth, and reduces subluxation of the femoral head. Another known feeding method, limit feeding, improves hip joint stability and reduces the incidence and severity of CHD by reducing the overall growth rate and bone maturation rate of pups. However, the known dog food compositions and feeding methods provide incremental amelioration of subluxation, and a need remains for dog food compositions and feeding methods which further reduce hip joint laxity and the severity of CHD.

It would be desirable to provide a method of reducing the incidence and severity of CHD and osteoarthritis by reducing hip joint laxity in dogs. It would also be desirable to provide such a method which is dietary in nature and easily practiced. It would be further desirable to provide a nutritionally balanced dog food composition which substantially improves hip joint congruity and ameliorates CHD and osteoarthritis. It would be still further desirable to provide such a dog food composition which, when fed to puppies during the early years of growth, reduces hip joint laxity and thus the severity of CHD in mature dogs.

SUMMARY OF THE INVENTION

These and other objects may be obtained with a nutritionally balanced dog food composition containing a dietary source of pyrophosphate. The dietary pyrophosphate source substitutes for other commonly used dietary phosphate sources which lack effect on hip joint laxity. For example, and in one embodiment of the dog food composition, about 2.0% sodium acid pyrophosphate, about 1.1% calcium carbonate and about 0.65% corn are together substituted for about 2.1% dicalcium phosphate and about 1.05% sodium bicarbonate. In use, a puppy is fed the dog food composition from weaning to about 2 years of age.

The dog food composition and feeding methods described herein reduce subluxation of the femoral head, thus slowing the development of CHD and osteoarthritis in dogs. Such methods are conveniently practiced by blending a dietary pyrophosphate source into a nutritionally balanced dog food composition, and then feeding the composition as substantially the sole diet to a puppy during the early stages of growth.

DETAILED DESCRIPTION

The nutritionally balanced dog food composition for reducing subluxation of the femoral head in the hip joint includes a source of dietary pyrophosphate blended into an admixture of ingredients which provides a nutritionally balanced food composition for dogs. The admixture may include a variety of suitable nutritious ingredients. The term dog food composition as used herein refers to any nutritionally balanced canned, dry or semi-moist dog food product such as those commonly commercially available in retail pet and grocery stores. In use, the dog food composition is fed to a puppy from weaning at about six weeks of age to about two years of age.

One embodiment of the dog food composition includes approximately 2.0% by weight of a dietary pyrophosphate source such as, for example, sodium acid pyrophosphate. The dietary pyrophosphate replaces other typical sources of dietary phosphate, such as dicalcium phosphate, which do not produce the same reduction of subluxation and amelioration of CHD. One theory explaining the ameliorating effect of dietary pyrophosphate on hip joint laxity is that by coating preformed bone crystal, pyrophosphate retards bone mineralization and growth rate, thereby reducing disparate growth between the feinoral head and acetabulum.

In alternative embodiments, the amount of dietary pyrophosphate or the type of pyrophosphate compound may be varied. Examples of suitable alternative pyrophosphate compounds include calcium pyrophosphate and tetrasodium pyrophosphate. In addition, sodium hexametaphosphate is thought to have the same effect as pyrophosphate compounds on hip joint laxity, and is a suitable substitute for a pyrophosphate compound. The amount of dietary pyrophosphate may range from about 0.1% to about 2.0% by weight. Although a precise dose-response relationship is not known, a practical upper limit for the pyrophosphate content is determined by the need to balance calcium. In particular, to avoid negative effects on bone mineralization, the percentage of dietary phosphorus should not exceed the percentage of dietary calcium.

The dog food composition as described herein further generally includes a nutritionally balanced mixture of proteinaceous and farinaceous ingredients, based on the assumption that the composition provides substantially the sole food intake for the dog. The dog food composition is not intended to be restricted to a specific listing of ingredients since such a listing is largely dependent on the desired nutritional balance of the dog food ration and also on the availability of ingredients to the manufacturer. In addition to the proteinaceous and farinaceous materials described above, the dog food composition generally may include vitamins, minerals, and other additives such as preservatives, emulsifiers and humectants. The nutritional balance, including for example the relative proportions of vitamins, minerals, fat, protein and carbohydrate, is determined according to dietary standards known in the nutrition art.

The proteinaceous material may include any material having a protein content of at least about 15% by weight including vegetable proteins such as soybean, cotton seed, and peanut; animal proteins such as casein, albumin, and meat tissue including fresh meat; and dried or rendered meals such as fish meal, poultry meal, meat meal, bone meal and the like. Other types of suitable proteinaceous materials include wheat gluten or corn gluten, and microbial proteins such as yeast. The minimum protein content of the food is varied according to the age and breeding status for the animal. For example, a nutritionally balanced food dog food composition for breeding females and puppies requires a minimum protein content of at least about 20% by weight on a 90% dry matter basis. A nutritionally balanced dog food composition for non-breeding and adult dogs requires a minimum protein content of about 12% by weight on a 90% dry matter basis.

The farinaceous material may be defined as any material having a protein content of less than about 15% by weight and containing a substantial proportion of starches or carbohydrates, including grains such as corn, milo, alfalfa, wheat, soy hulls, and other grains having low protein content. In addition to the proteinaceous and farinaceous materials, other materials such as dried whey and other dairy by-products, and other carbohydrates, may be added.

In addition, it has been shown that control of dietary anion gap improves hip joint stability in dogs. When dietary anion gap is defined as the level of sodium ions plus potassium ions minus chloride ions in the food composition, control of the balance at a level not greater than about 30 milliequivalents/100 grams of a dog food composition reduces hip joint laxity in dogs. To maximize the ameliorating effects of the dog food composition on hip joint stability, the dog food composition includes about 2.0% by weight of a dietary pyrophosphate source plus a dietary anion gap not greater than about 30 inilliequivalents/100 g food.

To make one embodiment of the dog food composition, the proteinaceous and farinaceous materials and additional desired materials, as chosen by availability and nutritional desirability, are combined to form an admixture, and the dietary pyrophosphate source is added in a dry form, such as, for example, granular, powdered or encapsulated form, and well blended throughout the admixture. The admixture is then transferred to a steam conditioner and subjected to steam and moisture to adjust the moisture content of the admixture to between about 20% and 40% by weight. The conditioned admixture is then extruded under conditions of elevated temperature and pressure to form a continuous strand of product. The product is segmented into discrete particles or pieces by a rotating cutting knife as the product is extruded. The particles or pieces are then conveyed to a forced air drying system and the moisture level is reduced to below about 10% by weight while the temperature of the particles or pieces is raised to about 140° F. The hot dried particles or pieces are then transferred by bulk conveyor to a spray chamber and dropped through the spray chamber. A plurality of spray heads located within the spray chamber, on both sides of the falling particles or pieces, spray a solution of animal fat onto the hot pieces or particles as they drop through the spray chamber.

The temperature of the pieces or particles within the forced air drying system may be adjusted to facilitate further processing. For example, a temperature of 140° F., as described above, facilitates coating of the pieces or particles with animal fat, where the melting point of the animal fat is below 140° F. The spray coated pieces or particles are collected at the bottom of the spray chamber and transported to a tumbling drum. The temperature of the tumbling drum is maintained above the melting point of the animal fat and the particles or pieces are tumbled until they have a substantially uniform surface coating of animal fat. The coated particles or pieces are then removed from the drum and cooled to ambient temperature. The resultant dry dog food composition has a moisture content of less than about 12% by weight, and a protein content above about 15% by weight on a 90% dry matter basis. In an alternate method, the dietary pyrophosphate source, in powdered, granulated or encapsulated form, may be applied to the hot particles or pieces after they have been coated with animal fat, for example by dusting onto the particles or pieces.

In use, a puppy owner purchases the dog food composition and feeds the composition to the puppy from weaning at about 6 to about 8 weeks of age to about 2 years of age. The owner may also continue to feed the composition beyond 2 years of age.

EXAMPLE 1

The study was done on Labrador Retrievers, a breed of dog with known risk for canine hip dysplasia. At 6–8 weeks of age, forty-four pups were blocked by litter, gender and body weight and randomly assigned to dietary treatment with either a control diet (R1) containing dicalcium phosphate, or a treatment diet (R2) in which sodium acid pyrophosphate and calcium carbonate were substituted for the dicalcium phosphate. The formulae for R1 and R2 are given in Table 1. Pups were individually fed ad libitum for 15 minutes, three times per day until 16 weeks of age. After 16 weeks of age, pups were fed individually once per day. The test was conducted over 104 weeks. Dietary anion gap was the same in both R1 and R2 diets and maintained at 27.5 mEq/100g.

TABLE 1

| Ingredient | R1 (weight %) | R2 (weight %) |
| --- | --- | --- |
| Soybean oil | 0.14 | 0.14 |
| Corn | 20.688 | 21.338 |
| Wheat | 30.0 | 30.0 |
| Sodium caseinate | 1.5 | 1.5 |
| L-lysine | 0.215 | 0.215 |
| Potassium chloride | 0.155 | 0.155 |
| Corn gluten meal | 12.1 | 12.1 |
| Soybean meal | 21.1 | 21.1 |
| Calcium carbonate | 0.84 | 1.94 |
| Dicalcium phosphate | 2.1 | 0.0 |
| Salt | 0.36 | 0.36 |
| Trace minerli | 0.2 | 0.2 |
| Animal fat | 8.85 | 8.85 |
| Sodium bicarbonate | 1.05 | 0.0 |
| Choline chloride (70) | 0.082 | 0.082 |
| Dog vitamin premix | 0.67 | 0.67 |
| Sodium acid pyrophosphate | 0.0 | 1.4 |
| Total | 100.0 | 100.0 |

Evaluation of the extent of hip joint subluxation was based on Norberg angle measurements taken from standard radiographs of properly positioned animals. Radiographs were taken under general anaesthesia. Norberg angle measurements were obtained using a protractor-like device to measure the closeness of fit between the femoral head (ball) and the acetabulum (hip socket). To obtain the Norberg angle from each radiograph, a line was drawn between the center of the femoral head of each hip and another line was drawn between the center of each femoral head and the cranial rim of the respective acetabulum. On each hip, the angle formed between these lines is the Norberg angle. Animals were evaluated at 16, 30, 42, 52, 78, and 104 weeks of age. Higher Norberg angles indicate superior hip joint fit, or congruity. Evaluation of whole body bone mineral density were based on Dual Energy X-ray Absorptiometry (DEXA) scan at 8, 17, 31, 43, 53, 79 and 105 weeks of age.

Table 2 gives mean Norberg angle measurements for animals at 16, 30, 42, 52, 78 and 104 weeks of age.

TABLE 2

| Age | Norberg Angles, ° R1 | Norberg Angles, ° R2 |
| --- | --- | --- |
| 16 weeks | 107.2 | 106.8 |
| 30 weeks | 106.5 | 109.6 |
| 42 weeks | 109.6 | 111.3 |
| 52 weeks | 110.2 | 112.9 |
| 78 weeks | 111.5 | 113.2 |
| 104 weeks | 112.6 | 113.3 |

At 30, 42, 52, and 78 weeks of age, a significant ($p<0.05$) improvement was observed in the mean Norberg angles of dogs fed R2 with dietary pyrophosphate, over the mean Norberg angles of dogs fed control ration R1.

Mean bone mineral density measurements from DEXA scans are given in Table 3 and show a significant ($p<0.05$) reduction in bone mineral density, which accompanied the improved Norberg angles. Bone mineral density was lower in R2-fed dogs than in R1-fed dogs at all ages tested except for 43 and 79 weeks.

The data shown in Tables 2 and 3 demonstrate reduced hip joint subluxation in the presence of slowed bone mineralization. The data cover the period of 0–9 months of age, the critical period for hip joint development.

TABLE 3

| Age | Avg. bone mineral density g/cm$^2$ R1 | Avg. bone mineral density g/cm$^2$ R2 | Significance (p value) |
| --- | --- | --- | --- |
| 8 weeks | 0.53 | 0.50 | 0.01 |
| 17 weeks | 0.75 | 0.70 | 0.01 |
| 31 weeks | 0.94 | 0.91 | 0.01 |
| 43 weeks | 0.94 | 0.93 | ns |
| 53 weeks | 0.95 | 0.92 | 0.02 |
| 79 weeks | 0.98 | 0.95 | 0.10 |
| 105 weeks | 100.0 | 0.98 | 0.05 |

Dietary analysis of pyrophosphate levels indicated that pyrophosphate was present in the R2 diet, and blood plasma pyrophosphate levels showed that pyrophosphate was being absorbed by the animals from the R2 diet. The results show that administration of dietary pyrophosphate during the first two years of growth reduces subluxation in canine coxofemoral joints, and also reduces the rate of bone mineralization, both of which contribute to the development of CHD.

EXAMPLE 2

Forty six Labrador Retriever and German Shepherd pups were blocked by litter, gender and body weight and randomly assigned to dietary treatment with either a control diet (R1) containing dicalcium phosphate, or a treatment diet (R2) in which calcium pyrophosphate and calcium carbonate were substituted for dicalcium phosphate. Both R1 and R2 were fed puppy-type diets formulated to contain approximately 12% by weight fat and approximately 25% by weight protein. Laboratory analysis of diets indicated that diets were made accurately.

Norberg angle measurements were taken at 5 and 10 weeks of age. Bone mineral density was evaluated by DEXA scan also at 5 and 10 weeks of age. No significant treatment effect was observed on Norberg angle measurements, but DEXA analyses indicated a significant lowering of bone mineral content and bone mineral density in R2-fed pups. The lack of treatment effects on hip joint measurements was expected because dietary treatment effects on canine hip dysplasia are almost never observed before 6 months of age. However, the results show that administration of dietary pyrophosphate reduces the rate of bone mineralization in growing Labrador Retriever and German Shepherd pups, an effect associated with long term amelioration of hip dysplasia symptoms.

In alternative embodiments of the dog food composition, a mixture of ingredients nutritionally balanced for cats or other animals afflicted with hip joint laxity may be used to encourage the development of proper hip conformation in those animals. In these alternative embodiments, the dietary pyrophosphate level is maintained at about 0.1% to about 2.0% by weight. For each such composition, the remaining ingredients and nutritional balance are determined by nutritional standards known in the art. In additional alternative embodiments, a dietary pyrophosphate source may be included in powdered, encapsulated form with other materials, such as vitamins and minerals.

The dog food composition and feeding methods described herein reduce subluxation of the coxofemoral joint in dogs, thus improving hip joint stability and retarding the development of CHD and osteoarthritis in dogs. The feeding methods are a simple, convenient and effective treatment for dogs known to be at risk for the development of CHD and osteoarthritis.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method of reducing hip joint laxity in a dog comprising the steps of:
    selecting a nutritionally balanced hip-laxity reducing dog food composition comprising a dietary pyrophosphate source wherein the dietary pyrophosphate content of the composition is about 0.1 to about 2.0% by weight of the composition; and
    feeding the composition to the dog.

2. The method in accordance with claim 1 wherein the nutritionally balanced dog food composition has a dietary anion gap of about 7 to about 30 mEq/100 g, wherein the dietary anion gap is determined according to the following formula:

$$\text{Dietary anion gap (mEq/100 g)} = \text{Sodium (mEq/100 g)} + \text{Potassium (mEq/100 g)} - \text{Chloride (mEq/100 g)}.$$

3. The method in accordance with claim 1 wherein the dietary pyrophosphate source comprises sodium acid pyrophosphate.

4. The method in accordance with claim 1 wherein the dietary pyrophosphate source comprises calcium pyrophosphate.

5. The method in accordance with claim 1 wherein the dietary pyrophosphate source comprises tetrasodium pyrophosphate.

6. The method in accordance with claim 1 wherein the step of selecting the nutritionally balanced dog food composition comprises the steps of:
    combining nutritious materials to form a nutritionally balanced admixture; and
    blending the source of dietary pyrophosphate into the admixture until the dietary pyrophosphate source is substantially blended through the admixture.

7. The method in accordance with claim 6 further comprising the steps of:
    adjusting the moisture content of the admixture to between about 20% and about 40% by weight percent;
    extruding the admixture to form a continuous strand of product;
    segmenting the strand of product into discrete pieces;
    drying the pieces to reduce the moisture content to below about 10% by weight percent; and
    coating the pieces with animal fat.

8. The method in accordance with claim 7 wherein the animal fat has a melting point and said step of coating the pieces with animal fat comprises:
    spraying animal fat onto the pieces;
    raising the temperature of the pieces above the melting point of the animal fat;
    tumbling the pieces so that the pieces have a substantially uniform coating of animal fat; and
    cooling the pieces to ambient temperature.

9. The method in accordance with claim 8 further comprising the step of dusting the dietary pyrophosphate source onto the pieces.

10. A method of reducing hip joint laxity in a dog comprising the steps of:
    selecting a nutritionally balanced hip-laxity reducing dog food composition comprising a dietary hexametaphosphate source wherein the dietary hexametaphosphate content of the composition is about 0.1 to about 2.0% by weight of the composition; and
    feeding the composition to the dog.

11. The method in accordance with claim 10 wherein the dog food composition has a dietary anion gap of about 7 to about 30 mEq/100 g, wherein the dietary anion gap is determined according to the following formula:

$$\text{Dietary anion gap (mEq/100 g)} = \text{Sodium (mEq/100 g)} + \text{Potassium (mEq/100 g)} - \text{Chloride (mEq/100 g)}.$$

* * * * *